US008821587B2

(12) United States Patent
Lanier et al.

(10) Patent No.: US 8,821,587 B2
(45) Date of Patent: Sep. 2, 2014

(54) APPARATUS FOR CONTROL OF A PROSTHETIC

(75) Inventors: Gregory R. Lanier, Manchester, NH (US); N. Christopher Perry, Manchester, NH (US); Andrew P. Pascoe, Windham, NH (US); Dirk A. Van der Merwe, Manchester, NH (US)

(73) Assignee: DEKA Products Limited Partnership, Manchester, NH (US)

( * ) Notice: Subject to any disclaimer, the term of this patent is extended or adjusted under 35 U.S.C. 154(b) by 0 days.

(21) Appl. No.: 12/027,116

(22) Filed: Feb. 6, 2008

(65) Prior Publication Data
US 2008/0243265 A1 Oct. 2, 2008

Related U.S. Application Data

(60) Provisional application No. 60/899,834, filed on Feb. 6, 2007, provisional application No. 60/963,638, filed on Aug. 6, 2007.

(51) Int. Cl.
| | | |
|---|---|---|
| *A61F 2/70* | (2006.01) | |
| *A61B 5/103* | (2006.01) | |
| *A61F 2/68* | (2006.01) | |
| *A61F 2/54* | (2006.01) | |
| *A61F 2/72* | (2006.01) | |
| *A61F 2/74* | (2006.01) | |
| *A61F 2/76* | (2006.01) | |
| *A61F 2/78* | (2006.01) | |
| *A61B 5/0488* | (2006.01) | |
| *A61B 5/00* | (2006.01) | |

(52) U.S. Cl.
CPC ... *A61F 2/68* (2013.01); *A61F 2/54* (2013.01); *A61F 2002/6827* (2013.01); *A61F 2002/6872* (2013.01); *A61F 2/72* (2013.01); *A61F 2002/701* (2013.01); *A61F 2002/704* (2013.01); *A61F 2002/705* (2013.01); *A61F 2002/707* (2013.01); *A61F 2002/741* (2013.01); *A61F 2002/762* (2013.01); *A61F 2002/7625* (2013.01); *A61F 2002/763* (2013.01); *A61F 2002/7635* (2013.01); *A61F 2002/764* (2013.01); *A61F 2002/7685* (2013.01); *A61F 2/78* (2013.01); *A61F 2002/7862* (2013.01); *A61B 5/0488* (2013.01); *A61B 5/1036* (2013.01); *A61B 5/4528* (2013.01)
USPC .............................. 623/24; 623/57; 600/587

(58) Field of Classification Search
USPC .................... 623/24–25, 30, 57–65
See application file for complete search history.

(56) References Cited

U.S. PATENT DOCUMENTS

| | | | |
|---|---|---|---|
| 43,590 | A | 7/1864 | Koeller |
| 975,029 | A | 11/1910 | Galvin |

(Continued)

FOREIGN PATENT DOCUMENTS

| | | |
|---|---|---|
| DE | 357699 | 8/1922 |
| DE | 19624215 C1 | 4/1997 |

(Continued)

OTHER PUBLICATIONS

Poulton et al., "Experience with the Intelligent Hybrid Arm Systems," MEC '02 TH Next Generation, Proceedings of the 2002 MyoElectric Controls/Powered Prosthetics Symposium Fredericton, New Brunswick, Canada: Aug. 21-23, 2002, Copyright University of New Brunswick, pp. 1-4 (all).*

(Continued)

*Primary Examiner* — Marcia Hoffman
(74) *Attorney, Agent, or Firm* — McCormick, Paulding & Huber LLP

(57) ABSTRACT

A prosthetic device control apparatus includes at least one sensor worn by a user. The sensor(s) determines a user's movement. A control module is in communication with the sensor(s). The control module communicates movement information to a prosthetic. A method for controlling a prosthetic device includes sensing a user's movement, communicating the movement through a control module to a prosthetic device; and controlling the movement of a prosthetic device.

15 Claims, 11 Drawing Sheets

(56) References Cited

U.S. PATENT DOCUMENTS

| | | |
|---|---|---|
| 1,745,959 A | 2/1930 | Steiner |
| 1,928,368 A | 9/1933 | Coffey |
| 2,070,960 A | 2/1937 | Phillips |
| 2,350,339 A | 6/1944 | Costa |
| 2,408,880 A | 10/1946 | Rebers |
| 2,516,791 A | 7/1950 | Motis et al. |
| 2,535,489 A | 12/1950 | Edwards |
| 3,654,855 A | 4/1972 | Longo |
| 3,745,998 A | 7/1973 | Rose |
| 3,763,773 A | 10/1973 | Clay |
| 3,779,654 A | 12/1973 | Horne |
| 3,883,900 A | 5/1975 | Jerard et al. |
| 3,935,795 A | 2/1976 | Hawley |
| 3,987,498 A | 10/1976 | Mason |
| 4,030,141 A * | 6/1977 | Graupe ............. 623/25 |
| 4,067,070 A | 1/1978 | Seamone et al. |
| 4,068,763 A | 1/1978 | Fletcher et al. |
| 4,155,169 A | 5/1979 | Drake et al. |
| 4,155,769 A | 5/1979 | Almagro |
| 4,209,860 A * | 7/1980 | Graupe ............. 623/25 |
| 4,253,449 A | 3/1981 | Arkans et al. |
| 4,258,441 A | 3/1981 | Bell |
| 4,413,895 A | 11/1983 | Lee |
| 4,521,924 A * | 6/1985 | Jacobsen et al. ........... 623/20.11 |
| 4,604,098 A | 8/1986 | Seamone et al. |
| 4,628,765 A | 12/1986 | Dien et al. |
| 4,657,003 A | 4/1987 | Wirtz |
| 4,674,351 A | 6/1987 | Byrd |
| 4,720,923 A | 1/1988 | Quinton et al. |
| 4,743,264 A | 5/1988 | Sherva-Parker |
| 4,792,338 A * | 12/1988 | Rennerfelt ............ 623/64 |
| 4,831,897 A | 5/1989 | Dobbs |
| 4,840,634 A | 6/1989 | Muller et al. |
| 4,842,608 A | 6/1989 | Marx et al. |
| 4,896,239 A | 1/1990 | Ghose |
| 4,903,536 A | 2/1990 | Salisbury, Jr. et al. |
| 4,908,037 A | 3/1990 | Ross |
| 4,946,421 A | 8/1990 | Kerley, Jr. |
| 5,018,513 A | 5/1991 | Charles |
| 5,088,171 A | 2/1992 | Suzuki |
| 5,108,456 A | 4/1992 | Coonan, III |
| 5,201,772 A | 4/1993 | Maxwell |
| 5,263,990 A | 11/1993 | Handal |
| 5,376,128 A | 12/1994 | Bozeman, Jr. |
| 5,405,405 A | 4/1995 | Love |
| 5,413,611 A | 5/1995 | Haslam, II et al. |
| 5,420,489 A | 5/1995 | Hansen et al. |
| 5,480,454 A | 1/1996 | Bozeman, Jr. |
| 5,501,498 A | 3/1996 | Ulrich |
| 5,611,774 A | 3/1997 | Postelmans |
| 5,673,367 A | 9/1997 | Buckley |
| 5,724,714 A | 3/1998 | Love |
| 5,796,229 A | 8/1998 | Akeel |
| 5,836,083 A | 11/1998 | Sangwan |
| 5,888,213 A | 3/1999 | Sears et al. |
| 5,910,720 A | 6/1999 | Williamson et al. |
| 6,129,476 A | 10/2000 | Berman et al. |
| 6,171,239 B1 * | 1/2001 | Humphrey ............. 600/372 |
| 6,244,644 B1 | 6/2001 | Lovchik et al. |
| 6,276,155 B2 | 8/2001 | Siman-Tov et al. |
| 6,286,225 B1 | 9/2001 | Schimmels et al. |
| 6,287,159 B1 | 9/2001 | Polakowski et al. |
| 6,301,964 B1 | 10/2001 | Fyfe et al. |
| 6,344,062 B1 * | 2/2002 | Abboudi et al. ............. 623/24 |
| 6,350,211 B1 | 2/2002 | Kolmar |
| 6,361,570 B1 | 3/2002 | Gow |
| 6,379,393 B1 | 4/2002 | Mavroidis et al. |
| 6,424,886 B1 | 7/2002 | Iversen et al. |
| 6,454,513 B1 | 9/2002 | Friederichs et al. |
| 6,494,039 B2 | 12/2002 | Pratt et al. |
| 6,585,774 B2 | 7/2003 | Dean, Jr. et al. |
| 6,597,965 B2 | 7/2003 | Graves et al. |
| 6,806,621 B2 | 10/2004 | Heim et al. |
| 6,876,213 B2 | 4/2005 | Beck |
| 6,896,704 B1 | 5/2005 | Higuchi et al. |
| 6,962,220 B2 | 11/2005 | Takenaka et al. |
| 6,987,374 B2 | 1/2006 | Iribe et al. |
| 7,001,434 B2 | 2/2006 | Van De Veen |
| 7,086,322 B2 | 8/2006 | Schulz |
| 7,144,430 B2 | 12/2006 | Archer et al. |
| 7,150,762 B2 | 12/2006 | Caspers |
| 7,744,551 B2 | 6/2010 | Pick et al. |
| 7,828,857 B2 * | 11/2010 | Farnsworth et al. ............ 623/64 |
| 7,837,474 B1 | 11/2010 | Nuccio-Youngs |
| 8,257,090 B1 | 9/2012 | Nuccio-Youngs |
| 2002/0099450 A1 | 7/2002 | Dean, Jr. et al. |
| 2002/0143405 A1 | 10/2002 | Davalli et al. |
| 2002/0170193 A1 | 11/2002 | Townsend et al. |
| 2003/0078674 A1 | 4/2003 | Phillips |
| 2003/0120183 A1 * | 6/2003 | Simmons ............. 600/595 |
| 2003/0139783 A1 | 7/2003 | Kilgore et al. |
| 2003/0149384 A1 | 8/2003 | Davis et al. |
| 2003/0181990 A1 | 9/2003 | Phillips |
| 2003/0196490 A1 | 10/2003 | Cardarelli |
| 2004/0030411 A1 | 2/2004 | Caspers |
| 2004/0049290 A1 | 3/2004 | Bedard |
| 2004/0054423 A1 | 3/2004 | Martin |
| 2004/0064286 A1 | 4/2004 | Levi et al. |
| 2004/0078091 A1 | 4/2004 | Elkins |
| 2004/0088057 A1 | 5/2004 | Bedard |
| 2005/0028392 A1 | 2/2005 | Campbell et al. |
| 2005/0066810 A1 | 3/2005 | Schulz |
| 2005/0119777 A1 | 6/2005 | Arbogast et al. |
| 2005/0156878 A1 | 7/2005 | Logue |
| 2005/0192676 A1 | 9/2005 | Sears et al. |
| 2005/0192677 A1 | 9/2005 | Ragnarsdottir et al. |
| 2005/0197717 A1 * | 9/2005 | Ragnarsdottir et al. ........ 623/24 |
| 2005/0234564 A1 | 10/2005 | Fink et al. |
| 2006/0006280 A1 | 1/2006 | Wood |
| 2006/0083454 A1 | 4/2006 | Ason et al. |
| 2006/0122710 A1 * | 6/2006 | Bedard ............. 623/24 |
| 2006/0167562 A1 | 7/2006 | Williams, III et al. |
| 2006/0167564 A1 | 7/2006 | Flaherty et al. |
| 2006/0189899 A1 * | 8/2006 | Flaherty et al. ............. 600/595 |
| 2006/0224247 A1 | 10/2006 | Clausen et al. |
| 2006/0224249 A1 | 10/2006 | Winfrey |
| 2006/0282175 A1 | 12/2006 | Haines et al. |
| 2007/0011919 A1 | 1/2007 | Case, Jr. |
| 2007/0021841 A1 | 1/2007 | Al-Temen et al. |
| 2007/0055383 A1 | 3/2007 | King |
| 2007/0186429 A1 | 8/2007 | Bonnet et al. |
| 2007/0191965 A1 | 8/2007 | Colvin et al. |
| 2007/0198098 A1 | 8/2007 | Roston et al. |
| 2007/0250179 A1 | 10/2007 | Latour |
| 2007/0282228 A1 | 12/2007 | Einav et al. |
| 2008/0009771 A1 | 1/2008 | Perry et al. |
| 2008/0045932 A1 | 2/2008 | Beau et al. |
| 2008/0215162 A1 | 9/2008 | Farnsworth et al. |
| 2008/0243266 A1 | 10/2008 | Haynes et al. |
| 2008/0252552 A1 | 10/2008 | Goebel et al. |
| 2008/0288088 A1 | 11/2008 | Langenfeld et al. |
| 2008/0312753 A1 | 12/2008 | Puchhammer |
| 2009/0000136 A1 | 1/2009 | Crampton |
| 2009/0038421 A1 | 2/2009 | Wilson et al. |
| 2009/0264799 A1 | 10/2009 | Bonutti et al. |
| 2009/0271000 A1 | 10/2009 | Altobelli et al. |
| 2010/0036455 A1 | 2/2010 | Sanders et al. |
| 2010/0081974 A1 | 4/2010 | Vess |
| 2010/0113994 A1 | 5/2010 | Ingimundarson et al. |
| 2011/0247321 A1 | 10/2011 | Streeter et al. |
| 2011/0257765 A1 | 10/2011 | Evans et al. |
| 2012/0123558 A1 | 5/2012 | Gill |
| 2012/0210590 A1 | 8/2012 | Ferrari |

FOREIGN PATENT DOCUMENTS

| | | |
|---|---|---|
| EP | 1159940 A2 | 12/2001 |
| EP | 1675212 A1 | 6/2006 |
| EP | 1916561 A2 | 4/2008 |
| EP | 2112740 A2 | 10/2009 |
| EP | 2133662 A2 | 12/2009 |
| FR | 2877227 A1 | 5/2006 |
| WO | 2004096502 A1 | 11/2004 |
| WO | 2005/087583 A1 | 9/2005 |

(56) References Cited

FOREIGN PATENT DOCUMENTS

| WO | 2006069264 A1 | 6/2006 |
|---|---|---|
| WO | 2008044207 A2 | 4/2008 |
| WO | 2008/098059 A2 | 8/2008 |
| WO | 2010/033098 A1 | 3/2010 |
| WO | 2010/120403 A2 | 10/2010 |
| WO | 2010120404 A2 | 10/2010 |
| WO | 2011036473 A1 | 3/2011 |

OTHER PUBLICATIONS

International Search Report for International Application No. PCT/US2008/053183 dated Jun. 17, 2008.
International Search Report for International Application No. PCT/US08/53187 dated Sep. 24, 2008.
International Search Report for International Application No. PCT/US08/53191 dated Jul. 31, 2008.
U.S. Appl. No. 12/026,971 on "Dynamic Support Apparatus", filed Feb. 6, 2008.
U.S. Appl. No. 12/027,141 on "Arm Prosthetic Device", filed Feb. 6, 2008.
International Preliminary Report on Patentability for International Application No. PCT/US2008/053183 dated Aug. 11, 2009.
International Preliminary Report on Patentability for International Application No. PCT/US2008/053191 dated Aug. 11, 2009.
International Preliminary Report on Patentability for International Application No. PCT/US2008/053187 dated Aug. 11, 2009.
International Search Report and Written Opinion from related International Application No. PCT/US2010/024316 dated Jun. 11, 2010 (14 pages).
Partial International Search Results from related International Application No. PCT/US2010/024326 dated Jul. 21, 2010 (6 pages).
Partial International Search Results from related International Application No. PCT/US2010/024334 dated Jul. 21, 2010 (7 pages).
U.S. Appl. No. 12/706,340 on Dynamic Support Apparatus and System, filed Feb. 16, 2010.
U.S. Appl. No. 12/706,575 on System, Method and Apparatus for Control of a Prosthetic Device, filed Feb. 16, 2010.
U.S. Appl. No. 12/706,609 on Arm Prosthetic Device, filed Feb. 16, 2010.
U.S. Appl. No. 12/706,471 on System, Method and Apparatus for Orientation Control, filed Feb. 16, 2010.
Search Report from corresponding International Appln. No. PCT/US2010/024326 dated Dec. 13, 2010 (7 pages).
Search Report from corresponding International Appln. No. PCT/US2010/024334 dated Dec. 16, 2010 (6 pages).
U.S. Appl. No. 13/088,035 on Dynamic Support Apparatus and System, filed Apr. 15, 2011.
U.S. Appl. No. 13/088,085 on System, Method and Apparatus for Control of a Prosthetic Device, filed Apr. 15, 2011.
U.S. Appl. No. 13/088,063 on Arm Prosthetic Device, filed Apr. 15, 2011.
International Search Report and Written Opinion from corresponding International Appln. No. PCT/US2009/069491 dated May 20, 2010 (13 pages).
Search Report from European Appln. No. 08729171.2 dated Aug. 29, 2011 (7 pages).
Search Report from European Appln. No. 08729175.3 dated Aug. 29, 2011 (5 pages).
Karoui M S et al., "Study and Design of a Loop Antenna for Application of Medical Telemetry" Industrial Technology, 2004, IEEE ICIT '04, IEEE International Conference on Hammamet, Tunsia, vol. 3, Dec. 8, 2004, pp. 1589-1595.
Yekeh K et al., "Wireless Communications for Body Implanted Medical Device" Microwave Conference, 2007, Asia-Pacific, IEEE, Piscataway, NJ, Dec. 11, 2007, pp. 1-4.
Partial International Search Report from corresponding international appln. No. PCT/US2011/041345 dated Mar. 5, 2012 (22 pages).
U.S. Appl. No. 13/323,094 entitled "Dynamic Support Apparatus and System", filed Dec. 12, 2011 (35 pages).
Partial International Search Report from corresponding international appln. No. PCT/US2011/041343 dated Nov. 24, 2011 (6 pages).
Partial International Search Report from corresponding international appln. No. PCT/US2011/031797 dated Dec. 8, 2011 (4 pages).
Search Report from corresponding European Appln. No. 08729167.0 dated Feb. 6, 2012 (6 pages).
Partial International Search Report from corresponding International Appln. No. PCT/US2011/041339 dated May 10, 2012 (6 pages).
Zaghloul et al., "Hybrid Reflector-Array Antenna Concept," Antennas and Propagation Society International Symposium 2006 IEEE, Jul. 9-14 2006, Virginia Polytechnic Institute and State University, Blacksburg, pp. 4311-4314, Conference Publications.
Quick Guide #3, C-Leg Patient Training Overview, Otto Bock, 2006, Training Pamphlet, pp. 1-4.
Graupe, "Control of an Artificial Upper Limb in Three Degrees of Freedom," Bulletin of Prosthetics Research, Fall 1975, pp. 25-39.
International Search Report and Written Opinion from corresponding International Appln. No. PCT/US2011/031797 dated Jun. 15, 2012 (14 pages).
Preliminary Report on Patentability from corresponding International Appln. No. PCT/US2011/031797 dated Oct. 9, 2012 (8 pages).
Examination Report from corresponding European Appln. No. 10714392.7 dated Oct. 25, 2012 (4 pages).
Jacobsen et al., "Development of the Utah Artificial Arm" IEEE Transactions on Biomedical Engineering, vol. BME-29, No. 4, Apr. 1982, pp. 249-269.
Partial International Search Report from corresponding international appln. No. PCT/US2013/039081 dated Aug. 29, 2013 (6 pages).
International Search Report and Written Opinion from corresponding International Appln. No. PCT/US2013/039081 dated Oct. 29, 2013 (15 pages).
Lake, et al., Evolution of Microprocessor Based Control Systems in Upper Extremity Prosthetics, Technology and Disability IOS Press, vol. 15 (2003), pp. 63-71 (6 pages).

* cited by examiner

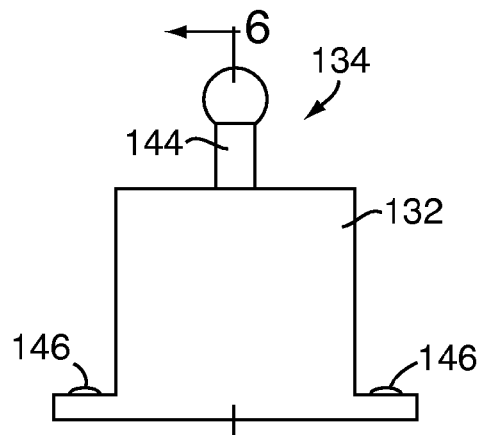
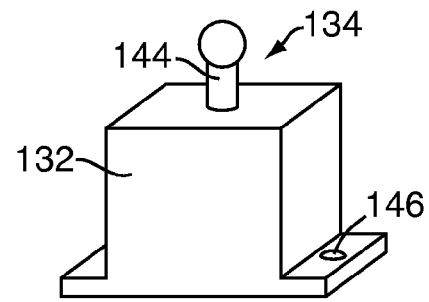
FIG. 5A
FIG. 5B
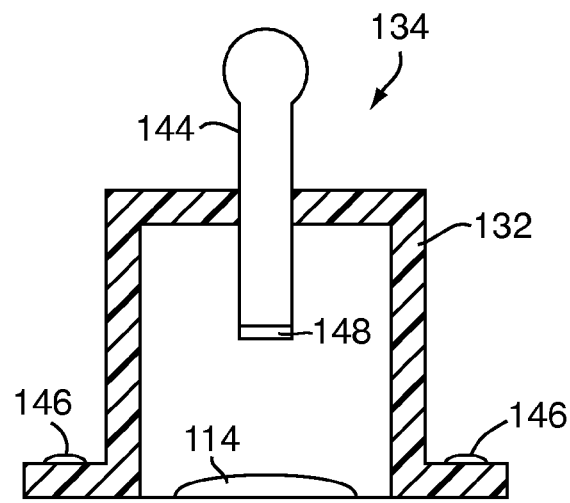
FIG. 6
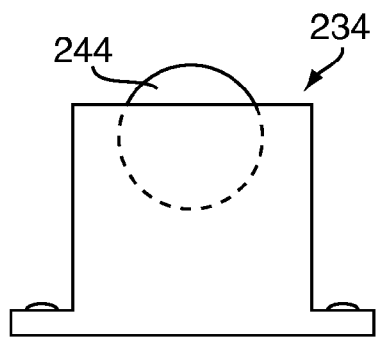
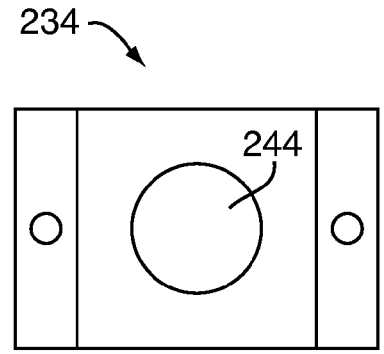
FIG. 7A
FIG. 7B

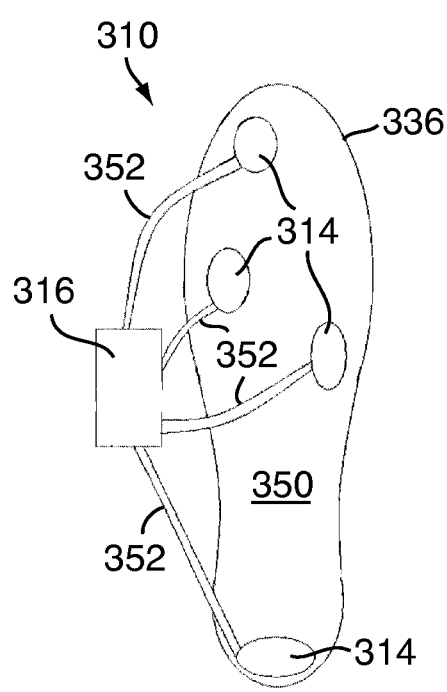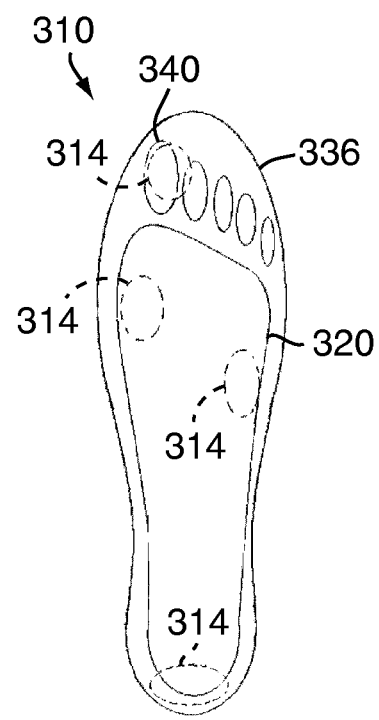
FIG. 8A    FIG. 8B
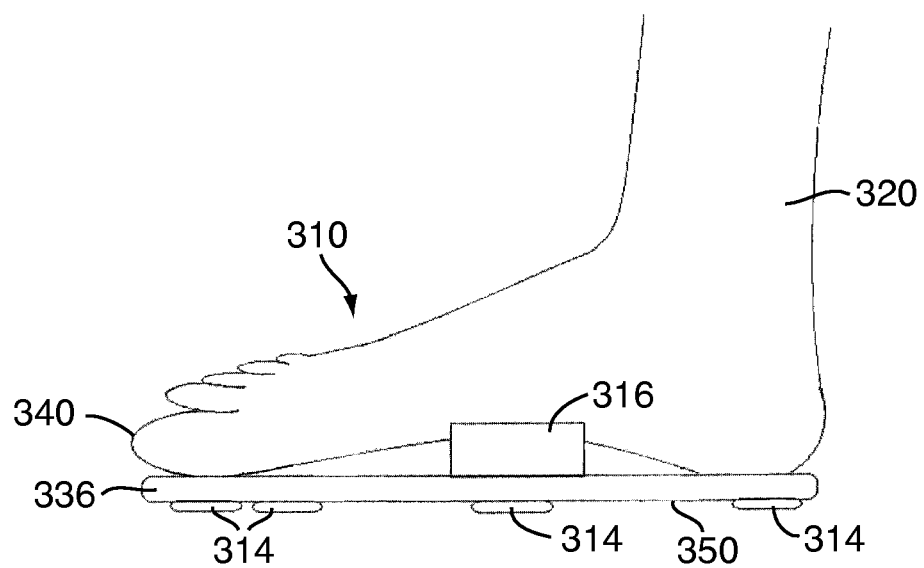
FIG. 9

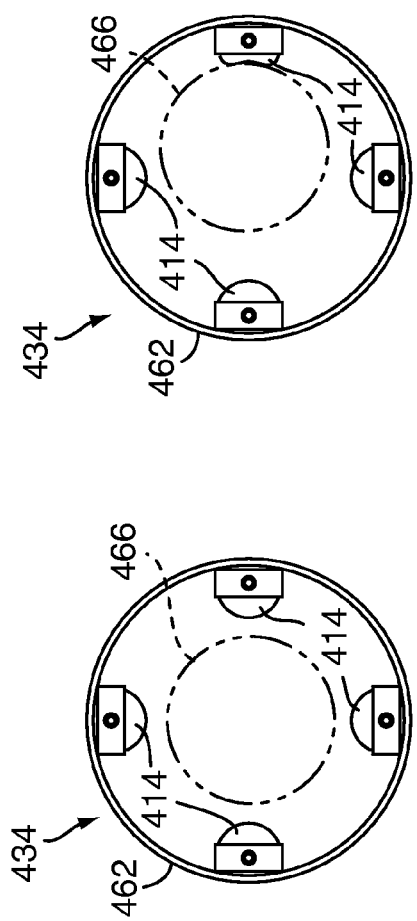
FIG. 19
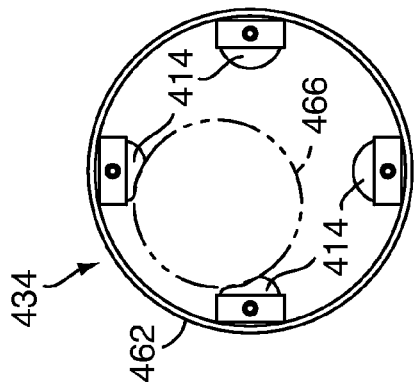
FIG. 20
FIG. 21
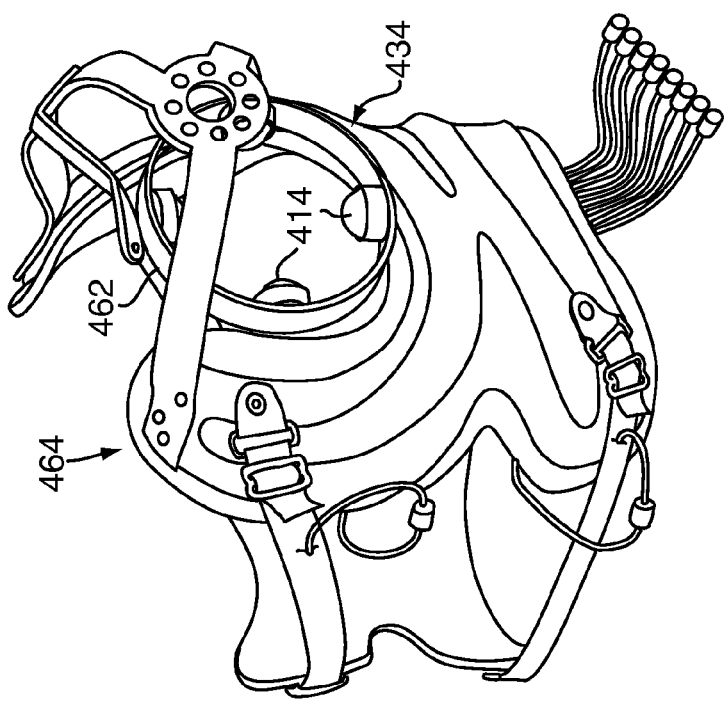
FIG. 18

APPARATUS FOR CONTROL OF A PROSTHETIC

CROSS REFERENCE TO RELATED APPLICATIONS

This application claims priority from and incorporates by reference in its entirety U.S. Provisional Patent Application Ser. No. 60/899,834, filed Feb. 6, 2007, entitled "Method And Apparatus For Control Of A Prosthetic" and U.S. Provisional Patent Application Ser. No. 60/963,638, filed Aug. 6, 2007, entitled "Foot Controller."

STATEMENT OF GOVERNMENT INTEREST

This invention was made with Government support under Contract Number W911NF-06-C-001 awarded by the U.S. Army RDECOM ACQ CTR. The Government has certain rights in the invention.

TECHNICAL FIELD

The present invention relates to control of a prosthetic and more particularly, to an apparatus and method for control of a prosthetic device.

BACKGROUND OF THE INVENTION

Many remote controls have been designed to manipulate robotic devices, mechanical devices, and virtual devices. There is a desire for a control system that may process user signals quickly and accurately while providing smooth directional and proportional control of associated objects.

SUMMARY OF THE INVENTION

In accordance with one aspect of the present invention, a prosthetic device control apparatus is disclosed. The control apparatus includes at least one sensor and at least one control module in communication with the sensor(s). The sensor(s) detects body input. The control module communicates movement information to a prosthetic.

In accordance with another aspect of the invention, the at least one sensor is disposed in footwear. In accordance with a further aspect of the invention, the control module is also disposed in footwear. In accordance with another aspect of the invention, the at least one sensor is disposed in a prosthetic support apparatus.

In accordance with another aspect of the invention, the control module is in wireless communication with the at least one sensor. In accordance with a further aspect of the invention, the control module is in wireless communication with the prosthetic.

In accordance with another aspect of the present invention, a method for controlling a prosthetic device is disclosed. The method comprises sensing body input. The method also comprises communicating the sensed body input to a control module. The method further comprises controlling movement of the prosthetic device based on the sensed body input.

These aspects of the invention are not meant to be exclusive and other features, aspects, and advantages of the present invention will be readily apparent to those of ordinary skill in the art when read in conjunction with the appended claims and accompanying drawings.

BRIEF DESCRIPTION OF THE DRAWINGS

These and other features and advantages of the present invention will be better understood by reading the following detailed description, taken together with the drawings wherein:

FIG. 5 is a side plan view and a side elevation view of a joystick, one embodiment of a motion reader for a foot controller;

FIG. 6 is a cross-sectional view of a joy stick, one embodiment of a motion reader for a foot controller;

FIG. 7 is a top plan view and a side plan view of a rollerball joy stick, another embodiment of a motion reader for a foot controller; and FIG. 8A is a top plan view of a one embodiment of a foot controller;

FIG. 8B is a top plan view of an embodiment of a foot controller, showing where the sensors are placed in relation to a user's foot;

FIG. 9 is a side elevation view of one embodiment of a foot controller;

FIG. 18 is a perspective view of the residuum controller of FIG. 16 incorporated into a prosthetic support apparatus;

FIG. 19 is a side view of the residuum controller of FIG. 16 in use;

FIG. 20 is a side view of the residuum controller of FIG. 16 in use;

FIG. 21 is a side view of the residuum controller of FIG. 16 in use;

DETAILED DESCRIPTION OF THE PREFERRED EMBODIMENTS

Figure 1:
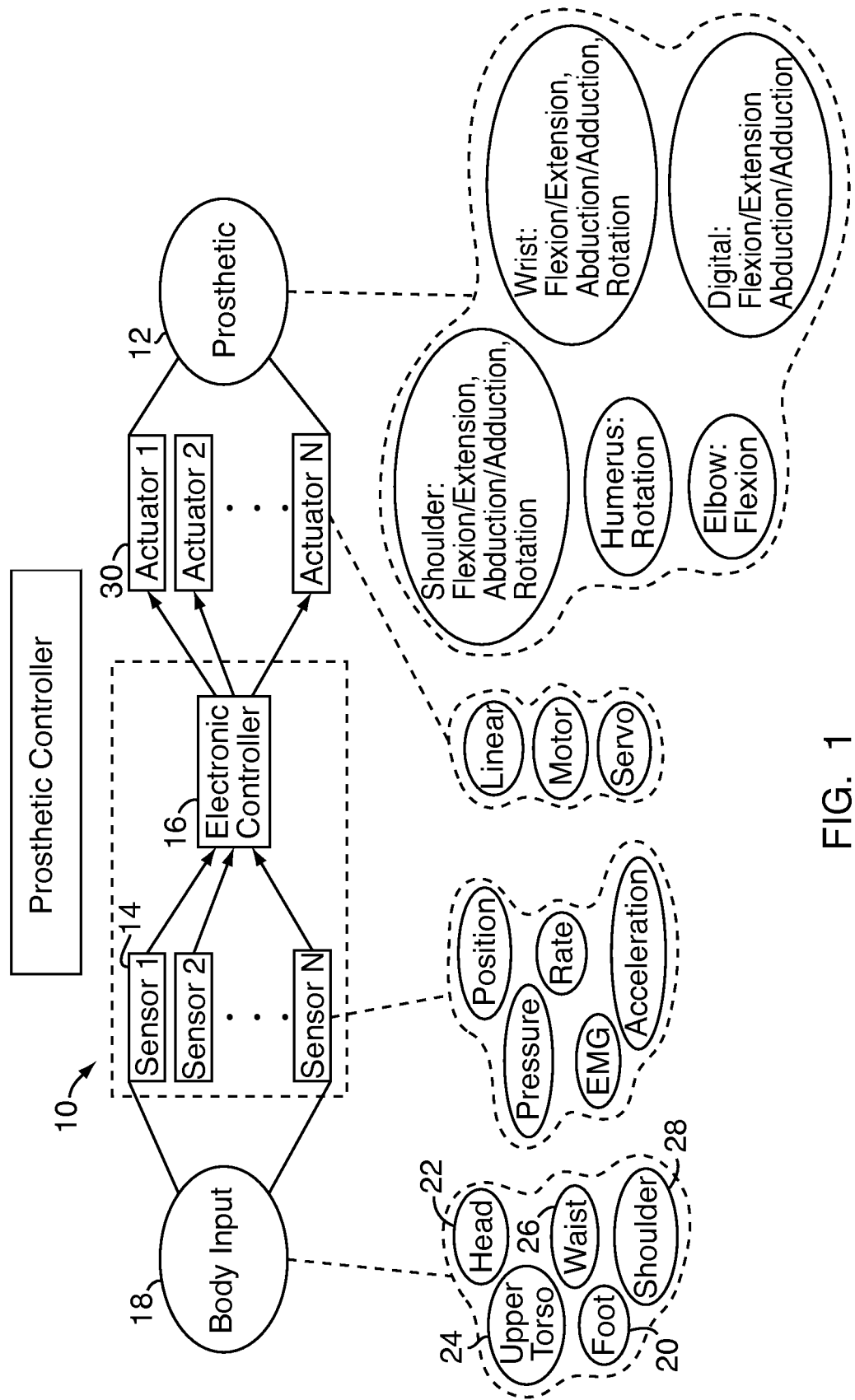
FIG. 1 is a schematic diagram of the prosthetic controller apparatus and function thereof.

Referring to FIG. 1, a schematic view of a control apparatus 10 for a prosthetic 12 is shown. The control apparatus 10 comprises one or more sensors 14 and an electronic controller 16.

The sensors 14 may be disposed at various locations on a user to sense body input 18 from the user. For example, the sensor 14 may be located to provide pressure information supplied by a foot 20 of the user. Similarly, sensors 14 may be positioned to measure body input 18 from other body parts of the user such as a head 22, an upper torso 24, a waist 26 or a shoulder 28. Sensors 14 may measure pressure, force, rate, or acceleration. Alternatively, the sensors 14 may be EMG electrodes.

The electronic controller 16 may be comprised of a single unit that collects data from the sensors 14, completes algorithms to translate the data into a desired movement, and sets and runs a plurality of prosthetic actuators 30 to achieve the desired movement of the prosthetic 20.

Alternatively, the electronic controller 16 may be comprised of two units that control the prosthetic 20, with a first unit setting and running the prosthetic actuators 30 and collecting physical inputs from the prosthetic 20, and a second unit collecting data from sensors 14, completing the algorithms to translate the data into the desired movement and sending the desired movement to the first unit.

Figure 2:
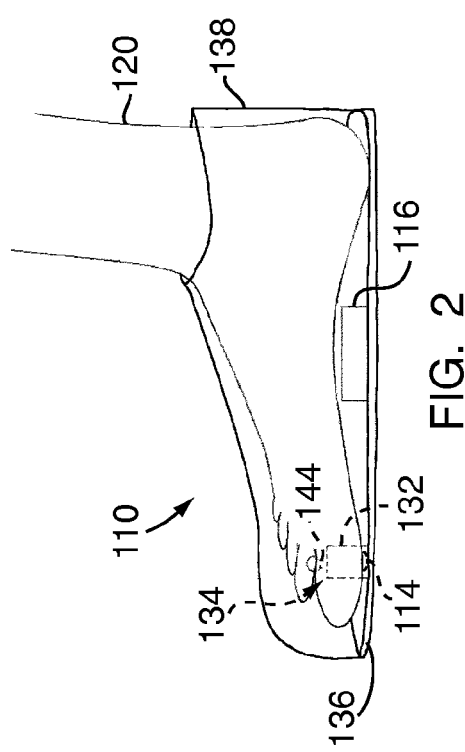
FIG. 2 is a side elevation view of one embodiment of a foot controller placed inside a shoe.

Referring to FIG. 2, one embodiment of the control apparatus 10 is shown as a toe controller 110, wherein the like numerals represent the like elements. Toe controller 110 comprises one or more inner sole sensors 114 and an electronic controller 116. In this embodiment, inner sole sensor 114 is positioned in a housing 132 of a joystick 134 and senses motion of the joystick 134, which has at least two degrees of freedom. The joystick 134 is placed on a sole 136 of footwear 138, and connected to the electronic controller 116.

Figure 4:
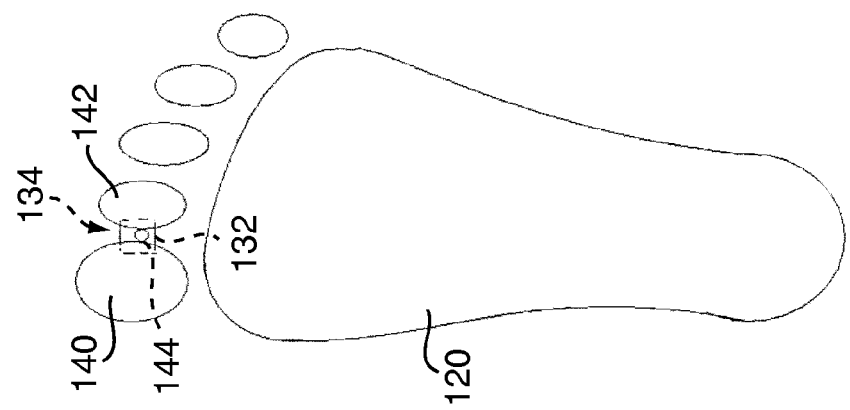
FIG. 4 is a top plan view of one embodiment of a foot controller.
Figure 3:
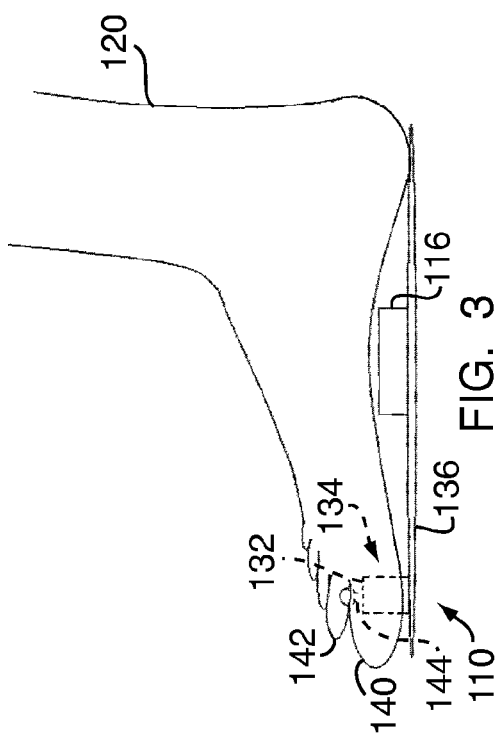
FIG. 3 is a side elevation of one embodiment of a foot controller.

Referring to FIGS. 3 and 4, the toe controller 110 locates the joystick 134 between a big toe 140 and an index toe 142 of a foot 120. Referring to FIGS. 5-6, the joystick 134 has a rod 144 centered through and operatively connected to the housing 132 such that rod 144 has two degrees of freedom. The sensor 114, as shown in FIG. 6 is positioned inside the housing 132 and below rod 144. While the dimensions of housing 132 may vary, in the exemplary embodiment, it has dimensions small enough to fit comfortably between the user's big toe 140 and index toe 142 and small enough to fit inside footwear 138. Housing 132 may also have mounts 146 so that joystick 134 may be attached to the sole 136 of footwear 138. The dimensions of rod 144 may vary, but in the exemplary embodiment, the rod 144 should at least be long enough for the user to grasp it between the big toe 140 and index toe 142. In the exemplary embodiment, the joystick 134 is thick enough that when the user presses against it, the joystick 134 will not break. Rod 144 may be made of stainless steel or other durable material. A magnet 148 may be placed at the end of rod 144 disposed inside the housing 132. The sensor 114 is connected by wires or wirelessly to an electronic controller 116, as shown in FIG. 2. Blue Tooth, RF communication, or other similar wireless connection may also be used to wirelessly connect sensor 114 to electronic controller 116. Sensor 114 detects the position of rod 144 and relays that information to the electronic controller 116. Sensor 114 may be a cross-axial sensor or other similar sensor.

In the embodiment shown in FIGS. 2-6, the user grips rod 144 with the big toe 140 and index toe 142 and presses against the rod 144 to control a direction of movement of an associated device, such as movement of a mouse on a computer screen, movement of a car, movement of a prosthetic limb, or movement of other similar remote-controlled devices. The user may also move rod 144 by placing the big toe 140 on top of rod 144 and pressing the rod 144 in the desired direction. As the user moves rod 144, sensor 114 detects displacement of the magnet 148 at the end of rod 144, and thus detects the direction the user is moving rod 144. That displacement information is then relayed to the electronic controller 116 which translates the movement of rod 144 into a desired movement of the associated device and communicates the displacement information to the associated device. The toe controller 110 has control of two degrees of freedom such as left and right, up and down, or forward and backward. The toe controller 110 may also be used as a discrete switch to open and close the associated device.

Referring to FIG. 7, in another embodiment, a ball joystick 234 includes a roller ball 244 instead of the rod 144. In this embodiment, the user may control the direction of the associated device by moving the big toe 140 across the roller ball 244. For example, if the ball joystick 234 is programmed to control left and right movement of a prosthetic arm, when the user presses the left side of roller ball 244, the prosthetic arm will move to the left. Similarly, when the user presses the right side of roller ball 244, the prosthetic arm will move to the right.

Referring to FIGS. 8A, 8B and 9, another alternative embodiment of the control apparatus 10 is shown as a foot controller 310. In this embodiment, an inner sole 336 includes sole sensors 314, positioned at various points on the inner sole 336. The sole sensors 314 may be of the type such as pressure sensors, force sensors, or the like. The sensors 314 are affixed to an underside 350 of the inner sole 336. The electronic controller 316 may be programmed to control various functions based on the input from each sole sensor 314. Although shown with multiple sole sensors 314, as few as one sole sensor 314 may be used, in which case the sole sensor 314 may function as a discrete on/off switch. Those skilled in the art will appreciate that by adding more sole sensors 314 to inner sole 336, the difficulty in independently controlling the movement of and pressure applied to each sensor 314 must be taken into consideration. Using two sole sensors 314, the foot controller 310 will have two degrees of freedom, either up and down, left and right, forward and backward, open and close or other similar discrete function. Using four sole sensors 314, the foot controller 310 will have four degrees of freedom with the ability to move forward, backward, left, and right or up, down, left, and right. Using six sole sensors 314, the foot controller 310 will have 6 degrees of freedom with the ability to move up, down, left, right, forward, and backward.

In the exemplary embodiment shown in FIGS. 8 and 9, foot controller 310 for a prosthetic arm has four sole sensors 314 placed on the underside 350 of the inner sole 336. FIG. 8B shows where the sole sensors 314 are in relation to a user's foot 320: one under the big toe 340, one under the left side of the foot 320, one under the right side of the foot 320, and one under the heel of the foot 320. The sole sensor 314 under the big toe 340 may control movement of the arm forward, the sole sensor 314 under the left side of the foot 320 may control movement of the arm to the left, the sole sensor 314 on the right side of the foot 320 may control movement of the arm to the right, and the sole sensor 314 under the heel may control movement of the arm backward.

Figure 10A:
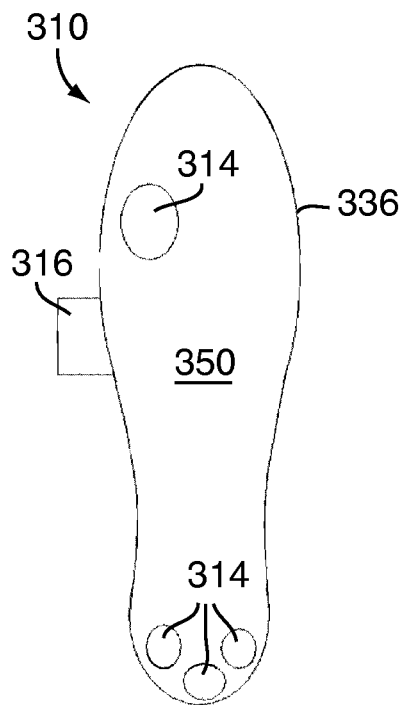
FIG. 10A is a top plan view of another embodiment of a foot controller.
Figure 10B:
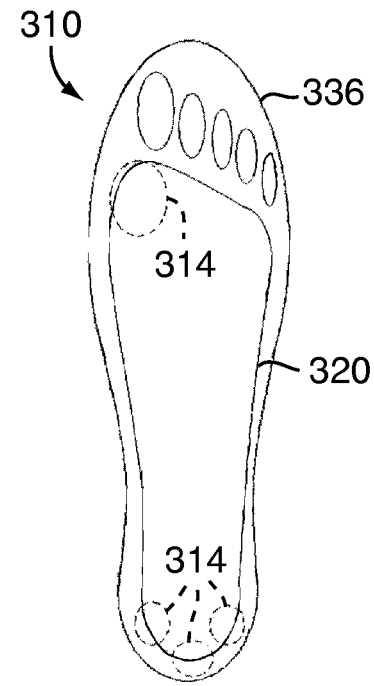
FIG. 10B is a top plan view of another embodiment of a foot controller, showing where the sensors are placed in relation to a user's foot.
Figure 11A:
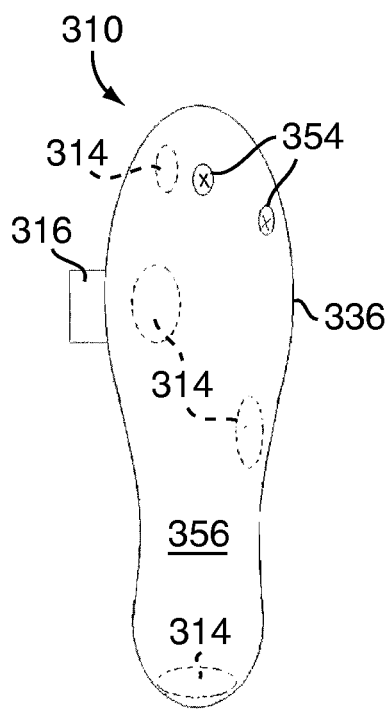
FIG. 11A is a top plan view of yet another embodiment of a foot controller.
Figure 11B:
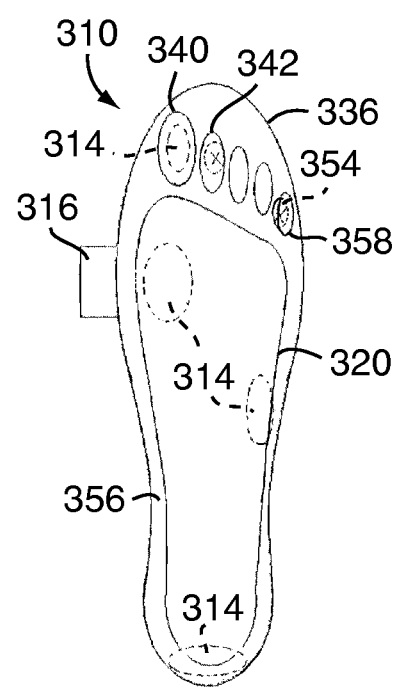
FIG. 11B is a top plan view of yet another embodiment of a foot controller, showing where the sensors are placed in relation to the user's foot.
Figure 12:
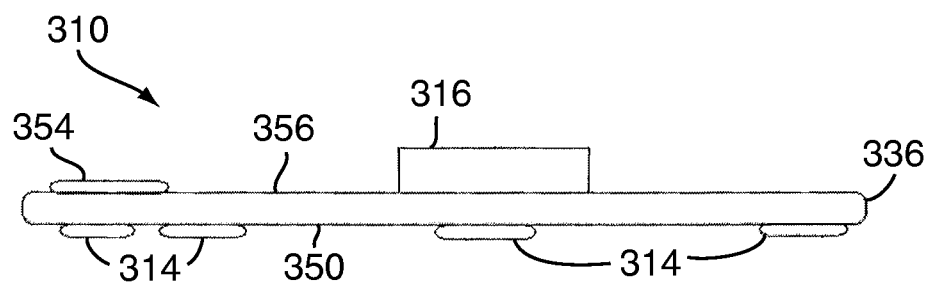
FIG. 12 is a side elevation view of another embodiment of a foot controller.
Figure 13:
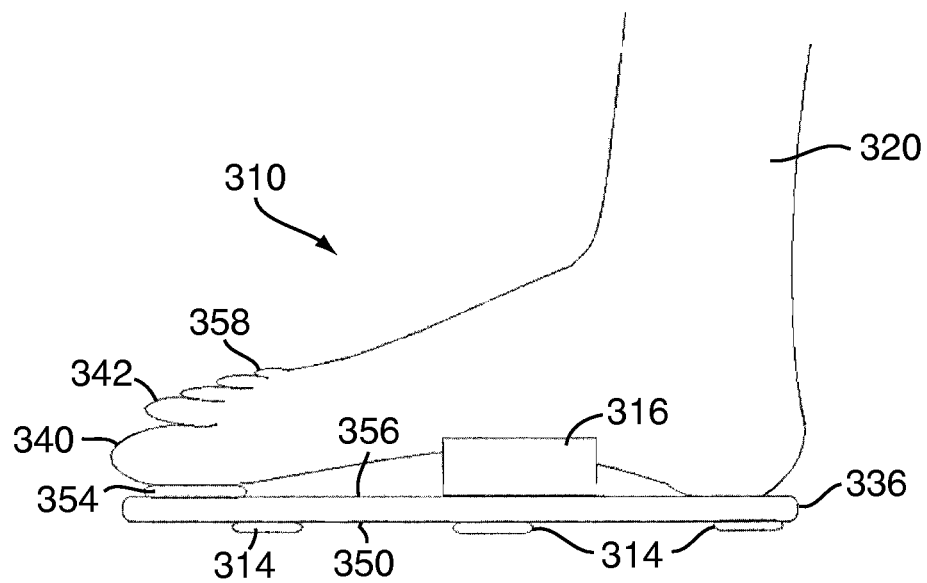
FIG. 13 is a side elevation view of another embodiment of a foot controller, showing where the sensors are in relation to a user's foot.

In alternative embodiments, the sole sensors 314 could be placed under other parts of the foot 320. For example, referring to FIGS. 10A and 10B, the underside 350 of the inner sole 336 might have one sole sensor 314 under the ball of the foot 320 and three sole sensors 314 under the heel of the foot 320.

Regardless of the sensor placement, in operation, the embodiments shown in FIGS. 8-10 operate in a similar fashion. The electronic controller 316 receives input from the sole sensors 314 and controls the associated device, such as a mouse on a computer screen, a robot, or a prosthetic limb. Wires 352, shown in FIG. 8A, may connect the sensors 314 to the electronic controller 316, which may be attached to the shoe. Alternatively, the sensors 314 may be wirelessly connected to the electronic controller 316 by a blue tooth device or other wireless communication.

In operation, as the user presses down on the sole sensors 314, a pressure or force pattern of the foot 320 is created, depending on the sole sensor placement. The sole sensors 314 measure the change in pressure applied by the user, and relay the pattern to the electronic controller 316. The electronic controller 316 translates the pattern into movement of the associated device being controlled in the form of the velocity change or the position change using an equation, for example, $\Delta P = \vec{V}_{to\ be\ changed}$ for velocity change or $\Delta P = X_{to\ be\ changed}$ for position. For example, with the foot controller 310 of the embodiment of FIGS. 8A and 8B that controls a prosthetic arm, if the user desires to move the prosthetic arm up, he might press down on the sole sensor 314 that is below the big toe 340. This creates a pressure pattern that is then relayed to the electronic controller 316 and translated into an upward movement of the arm. If the user desires to move the prosthetic arm down, he might press down on the sole sensor 314 under the heel, which creates a different pressure pattern that is relayed to the electronic controller 316 and translated into a downward movement of the arm.

Although described for exemplary purposes as providing only directional control, sole sensors 314 may also provide proportional control. For example, with sole sensors 314 that are pressure sensors or force sensors, the amount of pressure or force exerted on them may be translated into a speed at which the controlled device moves. Referring to FIGS. 8A, 8B and 9, for the foot controller 310 controlling a prosthetic arm, if the user desires to move the prosthetic arm quickly across the body from left to right, he might heavily press sole sensor 314 on the right side of inner sole 336. Alternatively, if the user desires to move the prosthetic arm slowly across the body from left to right, he might lightly press sole sensor 314 on the right side of inner sole 336. Accordingly, the movement output of the foot controller 310 may vary depending on the pressure or force applied by the user to the sole sensors 314, which is dissimilar to sensors that act only as switches, i.e., where no mater how hard the sensor is pressed, the output movement does not change.

With pressure sensors or force sensors, the user has better kinematic control of the prosthesis for smoother, less jerky, movements. The user is not limited to two movements of strictly up and down or left and right, but is rather able to control both the speed and direction of the movement. Additionally, the user may engage multiple sole sensors 314 simultaneously to give a combined motion (e.g. up and left). For example, in the embodiment shown in FIGS. 10A and 10B, the foot controller 310 has three sole sensors 314 under the heel that control the left, right, and backward movement of the prosthetic arm. As the user rolls the heel across the sole sensors 314 from right to left, the prosthetic arm will move smoothly in a similar sweeping backward movement. Without these sole sensors 314, the prosthetic arm would first have to move from left to right, stop, and then move backward, resulting in a choppy motion.

Referring to FIGS. 11A-13, in an alternative embodiment of the foot controller 310, the foot controller 310 may additionally have top sensors 354 placed on a topside 356 of the sole 336. This embodiment may have sole sensors 314 on the underside 350 of inner sole 336 as well as the top sensors 354 on the topside 356 of inner sole 336. In such an embodiment, top sensors 354 may act as discrete switches and may be placed under toes or other parts of the foot 320 that will not significantly affect the pressure or force readings of sensors 314 on the underside 350 of inner sole 336. For example and still referring to FIGS. 11A and 11B, when used to control a prosthetic arm, top sensors 354 act as mode switches, located on the topside 356 of inner sole 336 under the index toe 342 and little toe 358. The top sensor 354 under the index toe 342 may be pressed to signal the electronic controller 316 that the foot controller 320 is in an arm mode and will be moving the prosthetic arm. The top sensor 354 under the little toe 358 may then be pressed to switch to a hand grasping mode, which signals the electronic controller 316 that the foot controller 320 is being used to change the type of hand grasp. In other applications, such as using the foot controller 320 to drive a cursor on a computer screen, these top sensors 354 might be used to signal as left and right mouse buttons.

Figure 14:
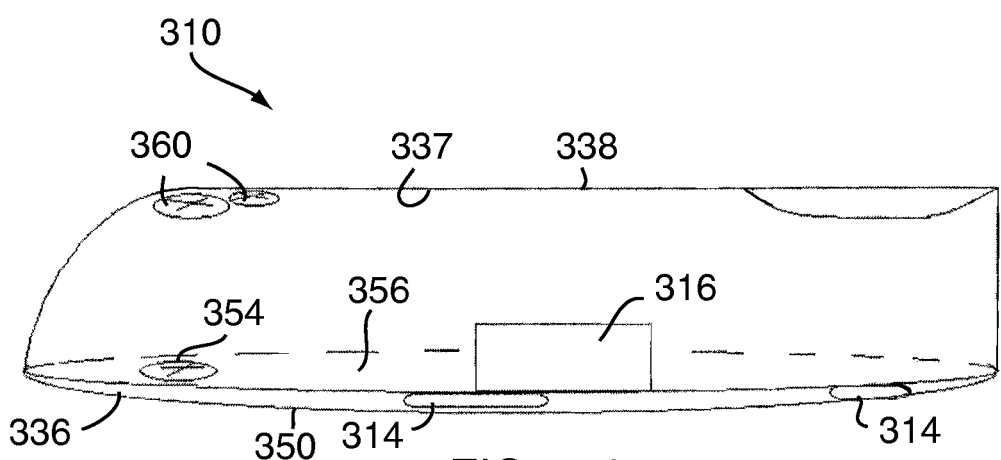
FIG. 14 is a side elevation view of yet another embodiment of a foot controller as it is placed inside a user's shoe.
Figure 15:
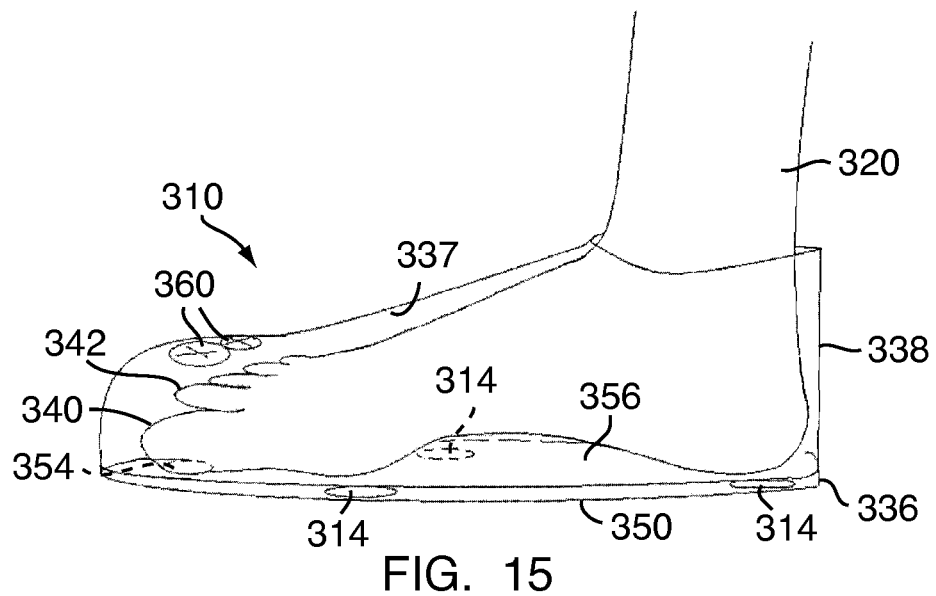
FIG. 15 is a side elevation view of yet another embodiment of a foot controller as it is placed inside a user's shoe, showing where the sensors are in relation to a user's foot.

Referring to FIGS. 14 and 15, another alternative embodiment of the foot controller 310 utilizing sole sensors 314, may additionally use shoe sensors 360, which may be placed above the toes on an inner portion of a roof 337 of footwear 338. In such an embodiment, shoe sensors 360 may act as discrete switches. For example, in addition to sole sensors 314 on the underside 350 of sole 336, the foot controller 310 may have the top sensor 354 on the top surface of sole 336 below the big toe 340 and shoe sensors 360 on the inner surface of the roof of the shoe 338 above the big toe 340 and index toe 342. The top sensor 354 and shoe sensors 360 may be programmed to switch modes. For example, pressing the big toe 340 up against the shoe sensor 360 may set the electronic controller 316 to arm mode to control the movement of the entire prosthetic arm. Alternatively, pressing the big toe 340 down against the top sensor 354 may set the electronic controller 316 to a wrist mode to control only the wrist of the prosthetic arm. In either mode, the sole sensors 314 could then be used to control the desired movement of the prosthetic. The shoe sensors 360 may also be used to control other features of a prosthetic, such as opening/closing a hand or acting as an on/off switch.

Although the foot controller 310 has been shown and described with respect to the detailed embodiments thereof, it will be understood by those skilled in the art that various changes in form and detail thereof may be made without departing from the spirit and scope of the invention. For example, the sensors may be attached to the inner lining of a sock or may be directly attached to a shoe.

Figure 16:
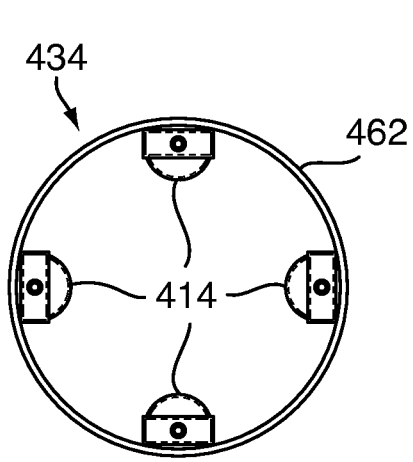
FIG. 16 is a side view of one embodiment of a residuum controller.
Figure 17:
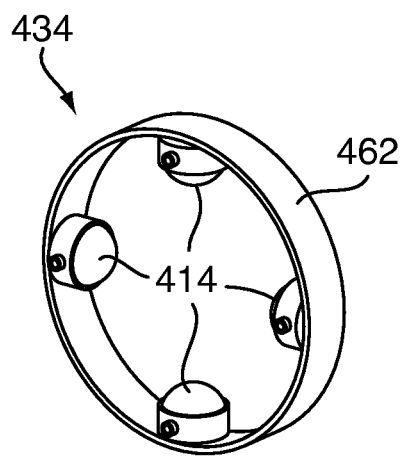
FIG. 17 is a perspective view of the residuum controller of FIG. 16.

Referring to FIGS. 16 and 17, in another alternative embodiment, the control apparatus 10 may be a shoulder controller including a residuum joystick 434, having a frame 462 and residuum sensors 414. Referring to FIG. 18, in this embodiment, the residuum joystick 434 may be attached to a prosthetic support 464 so that a user's residuum (not shown)

may extend into the residuum joystick 434. The user may then control the prosthetic by moving the residuum to activate the residuum sensors 414.

In this embodiment, as shown with four residuum sensors 414, the user may control the movement of the prosthetic in two degrees of freedom, such as vertical movement and horizontal movement. Referring to FIG. 19, a residuum 466 extends into the residuum joystick 434 having residuum sensors 414. As shown, the residuum 466 is not in contact with the residuum sensors 414, so the prosthetic will remain stationary. As shown in FIG. 20, the user may move the residuum 466 to engage the right residuum sensor 414, signaling the electronic controller (not shown) to move the prosthetic to the right. Similarly, as shown in FIG. 21, the user may move the residuum 466 forward and to the left, engaging two residuum sensors 414 to signal the electronic controller to move the prosthetic up and to the left.

The residuum sensors 414 may alternatively be used as discrete switches. For example, one residuum sensor may be used to switch between a mode in which an entire prosthetic arm is controlled and a mode in which only a hand of the prosthetic arm is controlled.

Another embodiment uses a control apparatus with kinematic mapping, sensing head and body movement, to control the prosthetic. The user moves the head and body in coordination to select a point in space where they desire the prosthetic to move. Head movement is slow, intentional and decoupled from a major function, which makes it ideal for prosthetic control.

The residuum input may provide physical feedback to a user. Thus, adding to spatial and other types of feedback a user may experience. Thus, the residuum input may enhance the control by the user. The residuum input may also be used for proportional and/or position control.

Figure 22:
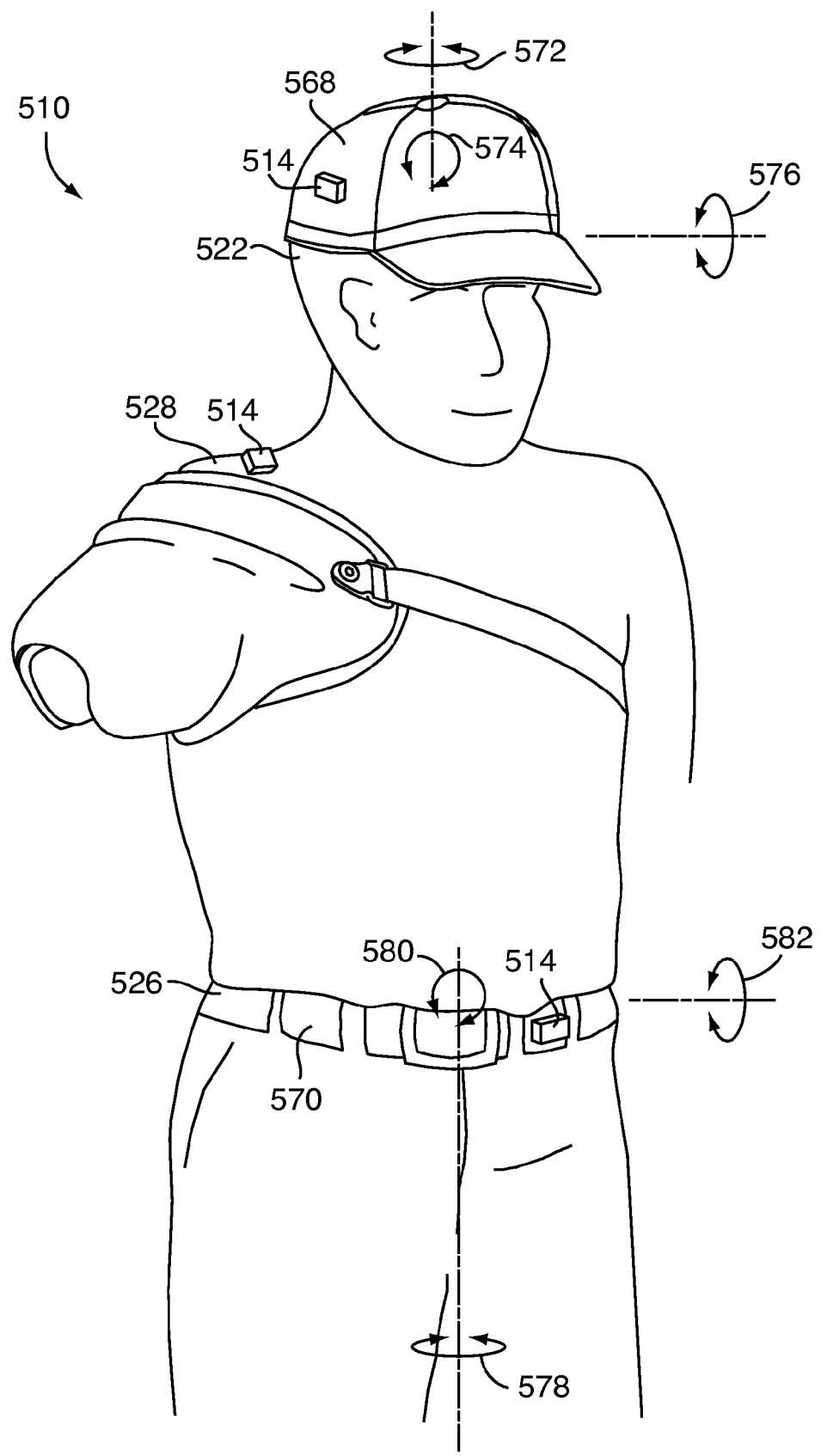
FIG. 22 is a front view of a kinematic mapping embodiment of the control apparatus.

Referring to FIG. 22, a kinematic mapping controller 510 features three body sensors 514 in three locations, the shoulder 528, the head 522, and the waist 526. In this embodiment, a hat 568 holds one body sensor 514. An alternative embodiment is to mount the head body sensor 514 above an ear as a wireless unit. One body sensor 514 may be incorporated into a belt 570 or a pack (not shown) strapped onto the midsection of the user. In this way, two body sensors 514 are on the body of the user and the other body sensor 514 is on the head.

This embodiment uses inertial sensors as body sensors 514. These three body sensors 514 may be used to detect up to six multiple degrees of freedom. Specifically, the body sensors 514 may detect head yaw 572, head roll 574, head pitch 576, torso yaw 578, torso roll 580 and torso pitch 582. Additionally, theses body sensors may detect x, y, and z plane positioning. These sensors may also act as velocity acceleration gyros, accelerometers, angular velocity and magnetometers. Although shown as inertial sensors, the body sensors 514 may also be shape sensors that may detect body flex.

Still referring to FIG. 22, this embodiment of the control apparatus 10 assumes a fixed point of rotation at the middle of the prosthetic hand and creates a reference sphere around the fixed point. User preference determines the location of the fixed point by allowing the user to zero out the system with specific body input sensed by body sensors 514, such as looking around. Then the user looks at a point, about which the sphere is created. By choosing where the fixed point of rotation is, the user customizes and orients the movement path. To select the fixed point and sphere, head 522 rotation specifies an angle and body lean or shoulder 528 rotation specifies radius.

Although the various embodiments of control apparatus have been described as separate controllers for simplicity, the embodiments may be used in combination to achieve the desired prosthetic control. For example, the foot controller may be used in conjunction with another control system, such as an inertial control system, a shoulder joystick, and/or an EMG control system.

A control method of the prosthetic arm includes a bulk movement and a finesse movement. Bulk movement includes movement of the prosthetic arm into the general vicinity desired by the user, which includes moving the shoulder, elbow, forearm, wrist and hand of the prosthetic arm, to the location desired. Finesse movement in this embodiment relates to manipulating an object and specifically relates to operating a prosthetic hand and a prosthetic wrist. Finesse movement is used to achieve wrist rotation, inflection and grasp, and to manipulate an object once the prosthetic arm has reached the desired location.

The finesse movement allows the prosthetic hand to grasp or grip an object. A grasp or grip refers to an orientation of the prosthetic hand's overall hand pattern. The grip must be physically activated to hold and manipulate the object.

The current method achieves the grip by using both bulk movement and finesse movement. The bulk movement allows the user to position the prosthetic arm to a specific point in a three-dimensional space (x, y, and z components). Once the prosthetic arm has reached the desired location, finesse movement allows the user to manipulate the prosthetic hand and grip the object.

Both bulk and finesse movements are determined using the various control apparatuses described herein. The user determines a point that they want the prosthetic arm to reach and relative to a control input, the prosthetic arm moves to that point in space. This type of bulk movement results in simultaneous degree of freedom movement.

For example, in an embodiment with head control, the head moves and controls one joint of the prosthetic arm, resulting in one action. The input is head movement; the output is movement of the prosthetic arm. Similarly, referring back to FIG. 15, in an embodiment having the foot controller 310, the user may apply pressure with different parts of the foot 320 to sensors 314, to control the bulk movement of the prosthetic arm. The user may then engage the shoe sensor 360 to switch from bulk movement to finesse movement, and then use sensors 314 to control the finesse movement of the prosthetic arm. This method allows the user to alternate between bulk movement and finesse movement.

In one embodiment, the control apparatus 10 controls shoulder deflection and extension, elbow flexion and extension, and humorous rotation to control the bulk movement of the prosthetic arm. Additionally, depending on the severity of the amputation, shoulder abduction and adduction may also be controlled for bulk movement. Wrist rotation, wrist flexion and extension, and a hand manipulator including the thumb and finger all combine for finesse movement. In finesse mode, pressure and force sensors measure the distribution of weight and may be used to detect input specific to the grasp. The distribution of weight on the foot sensors may deliver specific input allowing the electronic controller to select the desired grip. Alternatively, the head position may be used to select the grip.

Although described with regard to a shoulder disarticulation amputee, it should be understood by those skilled in the art that the control systems and methods described herein may be adapted to be used for any prosthetic strapped onto the body. For example, for an elbow joint disarticulation amputee (direct control of just elbow joint) finesse control may be used for wrist and hand manipulation.

In some embodiments, the electronic controller 16 for the prosthetic arm includes the following modes: an off mode, a home mode, a bulk mode, a finesse mode, and a hold mode. Any of the sensors 14 may be programmed for mode selection.

In the home mode, the prosthetic arm is in a preset location, such as by the side of the user and the prosthetic is not receiving any input and is not moving. In the bulk mode, the control apparatus 10 controls the bulk movement of the prosthetic arm. In the finesse mode, the control apparatus 10 controls the finesse movement of the prosthetic arm. The hold mode is a fixed position of the prosthetic arm. The hold position appears as though it is not receiving any input, but rather, the last position data is continuously sent to the prosthetic arm to actively maintain the position.

In an alternative embodiment of the hold mode, a hold command may be sent, rather than continually sending the same coordinates, freeing the system to do other functions instead of continuously calculating the last position. This improves the control apparatus by conserving power.

Figure 23:
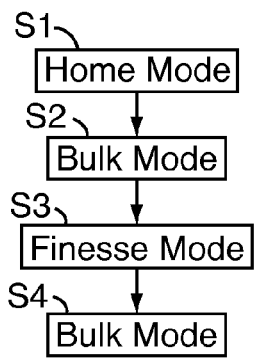
FIG. 23, is one method of control of the prosthetic.

Referring to FIG. 23, one embodiment of the control method of the control apparatus 10 includes operating the control apparatus in home mode S1, then in bulk mode S2, then in finesse mode S3, and then in bulk mode S4. This allows the user to move the prosthetic arm to the desired location, move the prosthetic hand and wrist to manipulate the object as desired, and then return the arm to home mode.

Figure 24:
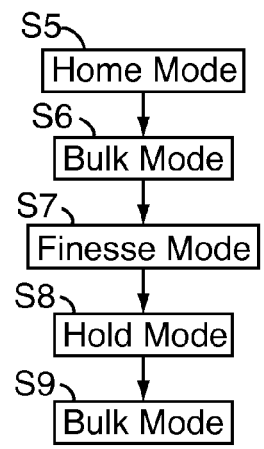
FIG. 24 is the method of control of the prosthetic according to FIG. 23 with an additional holding step.

Referring to FIG. 24, an additional embodiment may include operating the control apparatus 10 in home mode S5, then in bulk mode S6, then in finesse mode S7, then in hold mode S8, and then in bulk mode S9. This allows a user to move the prosthetic arm to the desired location and manipulate the object, then the user is able to hold the object in the desired position before the prosthetic arm is returned to home mode.

Figure 25:
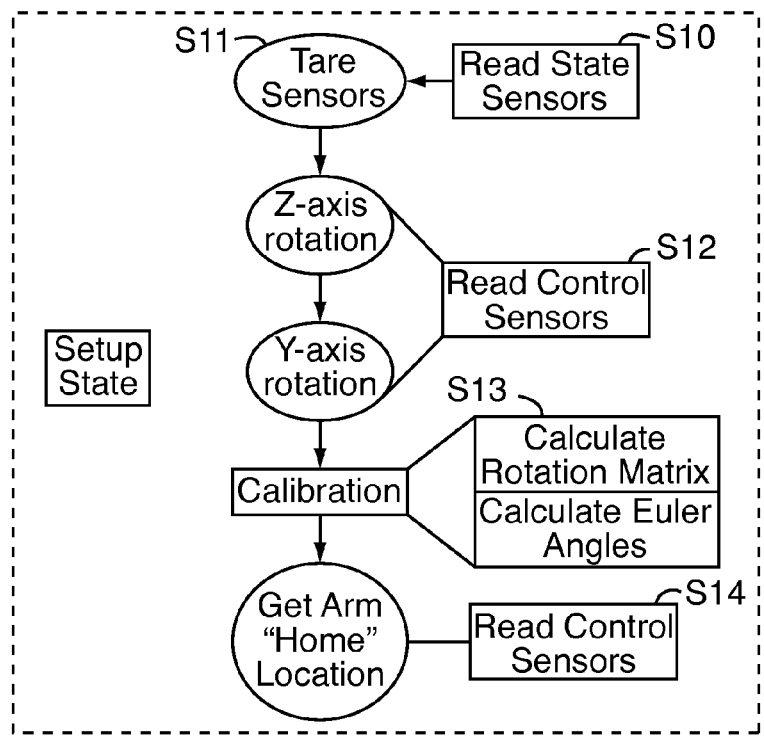
FIG. 25 is a schematic diagram of a control method during a setup state.

Referring to FIG. 25, in these embodiments having sensors 14, a person using the control apparatus puts the prosthetic arm on and simple setup state procedure is executed to quickly calibrate the prosthetic arm. State sensors in the prosthetic arm provide position information to the electronic controller 16 to identify the starting position of the prosthetic arm S10. The electronic controller 16 then tares the sensors 14 to zero them out, so that their rotations are in respect to their tarred position S11. The body sensors are then read to get the user's perceived Z and Y axis S12. A calibration step is then run where the Z axis is projected on the normal plane with the Y axis to get the X axis S13. The body sensors are then read again to identify the coordinates for the home mode S14. Then the control apparatus 10 is ready to be operated.

Figure 26:
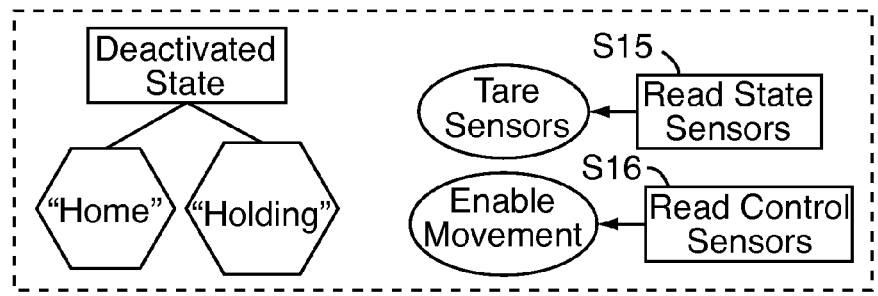
FIG. 26 is a schematic diagram of a control method during a deactivated state.

Referring to FIG. 26, when the control apparatus 10 is in a deactivated state such as in home mode or holding mode, prior to enabling movement, the transformation sensors in the prosthetic arm tare the body sensors to zero out, so that their rotations are in respect to their tarred position S15. The body sensors are then read to get the user's perceived Z and Y axis, and the Z axis is projected on the normal plane with the Y axis to get the X axis S16. Once the perceived axis are known, the sensors 14 are activated and may be used in bulk mode or finesse mode. The transformation sensors use the fixed point of the spherical mapping system and the lengths of each prosthetic arm component to determine when the arm has achieved the desired point in space.

Figure 27:
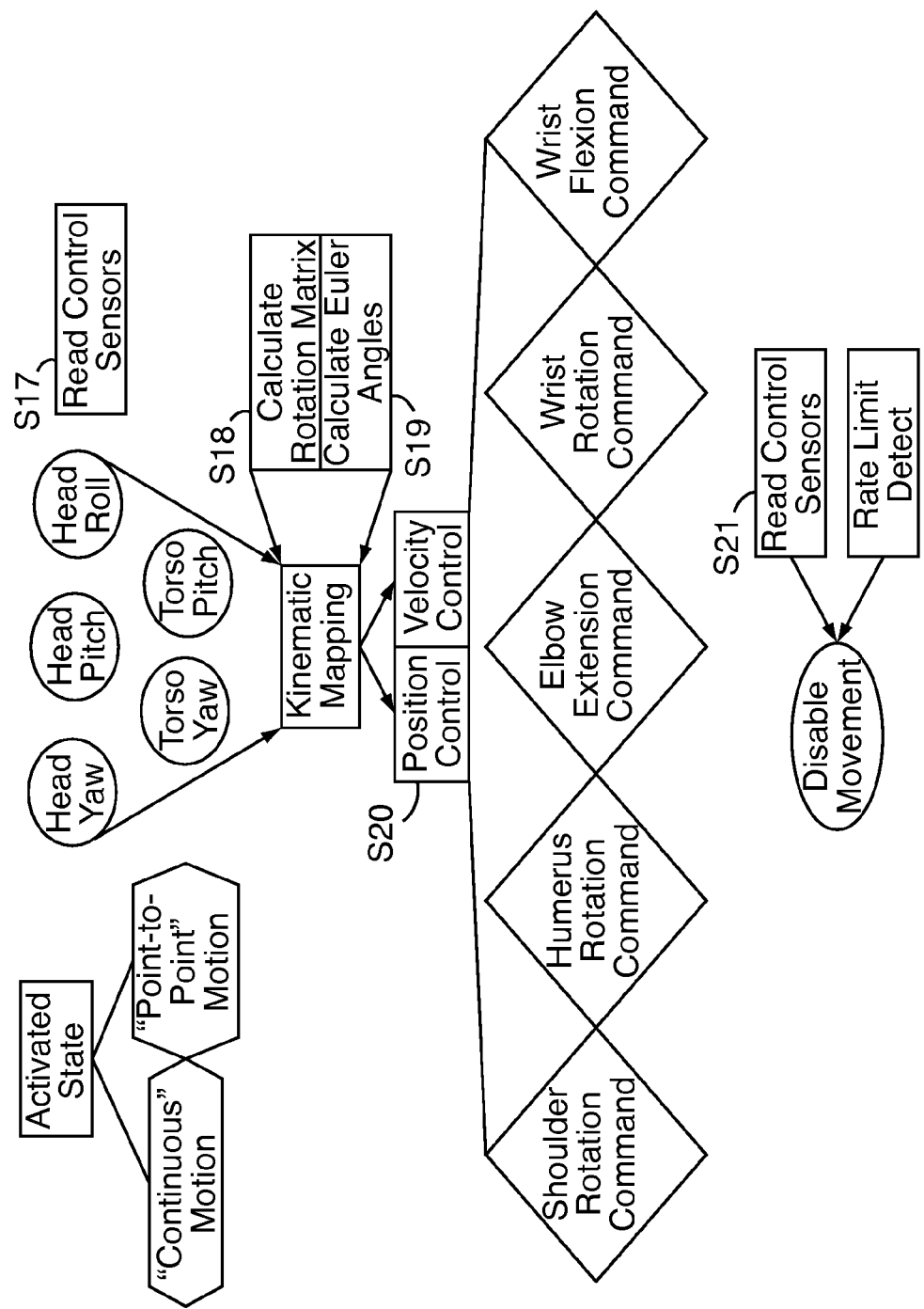
FIG. 27 is a schematic diagram of a control method during an activated state.

Referring to FIG. 27, a control method for embodiments using kinematic mapping, such as that shown in FIG. 22, is shown. When the sensors have been activated, the sensors identify the desired coordinates for the prosthetic arm to move to S17. Once the fixed point is specified, the electronic controller 16 goes through quadratic equation calculations to find the best mode of getting the target sphere in three-dimensional space to line up correctly S18. The electronic controller then goes through dot products to determine the necessary angles for the shoulder, elbow and humeral prosthetic movement S19. Based on those calculated angles, the arm is moved to reach the target sphere S20. Once the sensors determine that the target sphere has been reached, the arm movement is stopped S21.

In an alternative embodiment utilizing kinematic mapping, there is a click and go mode. This In the click and go mode, if the user wants to get to an object, they may look at a point in space where they want to go, and then engage a sensor that activates the click and go mode. In this mode: the body sensors determine where the head was looking and where the body leaned, and coordinates are sent directing the prosthetic to go to that place. Click and go mode uses the same sensor set for doing bulk movement as finesse movement. Once the bulk movement begins, the head will control the finesse movement.

In another embodiment, by using accelerometers and body sensors 514, the electronic controller 16 is able to identify the center of gravity in relation to the body sensor 514 on the shoulder. From that, the electronic controller 16 sending angle commands knows where the end of arm is and knows where the gravity vector with respect to the end of the arm is. Therefore, the controls rotate wrist with respect to the gravity vector to balance properly.

In an alternate embodiment using body sensors, the user could put the sensor on only their head, using the sensor to three-dimensionally map the desired movements. This would decrease the number of sensors required to control the prosthetic.

The control apparatus 10 may control sensitivity of movement in that the electronic controller 16 may vary the degree that sensor input is translated to movement output. Additionally, The sensor input may be required to meet a threshold value before movement output is sent to the prosthetic.

In an alternative embodiment, there may also be an arm swing mode, allowing the prosthetic arm to move in harmony with the body while walking. When the user is going to use the arm, it is in the home/off position, and swing mode may be activated by engaging a sensor 14 or by detecting a specific head motion with the body sensor 514.

Switching modes may be accomplished by engaging sensors 14 acting as discrete switches, by specific body motion such as ticks or head movement, by standard EMG signals using EMG electrodes, by shoulder or back movements, or by any other similar switching mechanism that may be programmed into the control apparatus 10.

The sensors 14 may be disposed in various locations for providing body input 18 to control the movement of the prosthetic device 12, such as in footwear. The control apparatus 10 may utilize wireless communication between the sensors 14, electronic controller 16 and prosthetic device 12, simplifying the prosthetic device control apparatus 10 for the user. The sensors 14 may act as discrete switches to control operational modes of the prosthetic device. The control apparatus 10 may move the prosthetic device 12 proportionally to the body input 18 sensed by the sensors 14. The sensors 14 may be disposed in a prosthetic support apparatus 464, allowing user to provide body 18 input to the sensors 14 with the residuum 466.

Each sensor 14 may sense a variety of body input such as pressure and rate of pressure change. Therefore, body input 18 from one sensor 14 may be translated by the electronic controller 16 into multiple forms of movement information, such as direction and speed of movement.

Although the current embodiment targets the shoulder disarticulation amputee, the current methods and systems may be broken down for use with the trans-humerus and trans-radial amputees. If there is humeral rotation, the bulk movement is only elbow flexion. Depending on the user's degree of amputation, the bulk mode changes or is removed from the method and apparatus if bulk is not required. Some embodiments will use both bulk and finesse, other embodiments, just finesse and still other embodiments will use a different level of bulk along with the finesse mode.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention.

What is claimed is:

1. A prosthetic device control apparatus comprising:
   at least one inertial sensor adapted to be worn by a user, the at least one inertial sensor detecting body movements that are indicative of a desired movement of a prosthetic device; and
   a control module in communication with the at least one sensor and receiving at least one signal based on the detected body movements therefrom, the control module having a plurality of user selectable control modes, each user selectable control mode defining a different motion for the prosthetic device, the plurality of user selectable control modes including at least a bulk control mode for moving the prosthetic device into a desired position and a finesse control mode for manipulating a prosthetic hand of the prosthetic device once the prosthetic device is in the desired position;
   wherein the control module commands a first plurality of prosthetic actuators to control shoulder movement, elbow movement and humeral rotation of the prosthetic device based on the detected body movements indicated by the at least one signal from the at least one inertial sensor to achieve bulk movement of the prosthetic device when the bulk control mode has been selected, thereby moving the prosthetic device into the desired position through a combination of shoulder movement, elbow movement and humeral rotation of the prosthetic device; and
   wherein the control module commands a second plurality of prosthetic actuators that is different than the first plurality of actuators to control wrist movement and hand movement of the prosthetic device based on a signal from the same at least one inertial sensor used to control the first plurality of actuators to achieve finesse movement of the prosthetic device when the finesse control mode has been selected, thereby manipulating the prosthetic hand through a combination of wrist movement and hand movement of the prosthetic device;
   wherein the at least one inertial sensor detects at least one of x, y or z plane positioning.

2. The prosthetic device control apparatus according to claim 1, wherein the control module is in wireless communication with the at least one inertial sensor.

3. The prosthetic device control apparatus according to claim 1, wherein the control module is in wireless communication with the prosthetic device.

4. The prosthetic device control apparatus according to claim 1, wherein the control module controls movement of the prosthetic device to be substantially proportional to the body movement detected by the at least one sensor.

5. The prosthetic device control apparatus according to claim 1 wherein the at least one inertial sensor is an acceleration gyro.

6. The prosthetic device control apparatus according to claim 1 wherein the at least one inertial sensor is an accelerometer.

7. The prosthetic device control apparatus according to claim 1 wherein the at least one inertial sensor wirelessly communicates information to said control module.

8. A prosthetic device control apparatus comprising:
   a sensor adapted to be worn by a user, the sensor detecting body movement in at least two degrees of freedom; and
   an electronic controller that is operably connected to the sensor and receiving at least one signal based on the detected body movement therefrom, the electronic controller having a plurality of user selectable control modes, each user selectable control mode defining a different motion for the prosthetic device, the plurality of user selectable control modes including at least a bulk control mode for moving the prosthetic device into a desired position and a finesse control mode for manipulating a prosthetic hand of the prosthetic device once the prosthetic device is in the desired position, the electronic controller controlling movement of the prosthetic device in at least two degrees of freedom based on the at least one signal and based on a selected control mode of the plurality of user selectable control modes, the movement of the prosthetic device being proportionate to the body movement detected by the sensor;
   wherein the control provided by the electronic controller based upon a given signal received from the sensor changes between commanding a first plurality of actuators to control shoulder movement, elbow movement and humeral rotation of the prosthetic device based on the detected body movement indicated by the given signal received from the sensor to achieve bulk movement of the prosthetic device when the bulk control mode has been selected, thereby moving the prosthetic device to the desired position through a combination of shoulder movement, elbow movement and humeral rotation of the prosthetic device, and commanding a second plurality of actuators that is different than the first plurality of actuators to control wrist movement and hand movement of the prosthetic device based on a signal from the same sensor used to control the first plurality of actuators to achieve finesse movement of the prosthetic device when the finesse control mode has been selected, thereby manipulating the prosthetic hand through a combination of wrist movement and hand movement of the prosthetic device, upon a mode change between the bulk control mode and the finesse control mode of the plurality of user selectable control modes.

9. The prosthetic device control apparatus according to claim 8, wherein the electronic controller is in wireless communication with the sensor.

10. The prosthetic device control apparatus according to claim 8, wherein the electronic controller is in wireless communication with the prosthetic device.

11. The prosthetic device control apparatus according to claim 8, wherein the sensor is an inertial sensor.

12. The prosthetic device control apparatus according to claim 11, wherein the sensor detects at least one of x, y or z plane positioning.

13. The prosthetic device control apparatus according to claim 11, wherein the sensor is an acceleration gyro.

14. The prosthetic device control apparatus according to claim 11, wherein the sensor is an accelerometer.

15. The prosthetic device control apparatus according to claim 11, wherein the sensor wirelessly communicates information to said electronic controller.

* * * * *